(12) United States Patent
Hill et al.

(10) Patent No.: US 12,378,979 B2
(45) Date of Patent: Aug. 5, 2025

(54) DYNAMIC RECRUITMENT MODULATION IN SYSTEMS UTILIZING VARIABLE RECRUITMENT

(71) Applicant: Adaract Technologies, Ltd., Reno, NV (US)

(72) Inventors: Joseph Hill, Reno, NV (US); Francis Budu-Manuel, Reno, NV (US)

(73) Assignee: ADARACT TECHNOLOGIES, LTD., Reno, NV (US)

( * ) Notice: Subject to any disclaimer, the term of this patent is extended or adjusted under 35 U.S.C. 154(b) by 104 days.

(21) Appl. No.: 18/354,000

(22) Filed: Jul. 18, 2023

(65) Prior Publication Data

US 2023/0380996 A1  Nov. 30, 2023

Related U.S. Application Data

(63) Continuation-in-part of application No. 17/689,352, filed on Mar. 8, 2022, now Pat. No. 11,719,263.

(60) Provisional application No. 63/165,411, filed on Mar. 24, 2021.

(51) Int. Cl.
*F15B 15/10* (2006.01)
*A61F 2/66* (2006.01)
*A61F 2/74* (2006.01)
*F15B 1/04* (2006.01)

(52) U.S. Cl.
CPC .......... *F15B 15/103* (2013.01); *A61F 2/6607* (2013.01); *A61F 2/741* (2021.08); *A61F 2/742* (2021.08); *A61F 2/748* (2021.08); *F15B 1/04* (2013.01); *F15B 2211/65* (2013.01)

(58) Field of Classification Search
CPC ...... F15B 15/103; A61F 2/6607; A61F 2/741; A61F 2/742; A61F 2/748; A61F 2/70; A61F 2/74; A61F 2002/407; A61F 2002/7635
See application file for complete search history.

(56) References Cited

U.S. PATENT DOCUMENTS

| 4,190,081 A | 2/1980 | Coles |
| 4,792,173 A | 12/1988 | Wilson |
| 4,794,912 A | 1/1989 | Lia |

(Continued)

OTHER PUBLICATIONS

U.S. Appl. No. 17/689,352, Non-Final Office Action Mailed Aug. 1, 2022, 20 pp.

(Continued)

*Primary Examiner* — Dustin T Nguyen
(74) *Attorney, Agent, or Firm* — Jared L. Cherry; PCFB, LLC

(57) ABSTRACT

The present disclosure relates to variable recruitment actuator systems and related methods. In one embodiment, a variable recruitment actuator system utilizes a central hydraulic pump, an accumulator, a plurality of variable recruitment actuators, and a pressurized reservoir of hydraulic fluid to provide highly efficient hydraulic regenerative energy harvesting in systems requiring both eccentric and concentric motion. In another embodiment, a powered prosthetic or orthotic device, or a legged robot, utilizes a system as previously described to capture energy from the eccentric motion of the knee joint to provide concentric motion of both the knee and ankle joints later on in a gait cycle.

18 Claims, 13 Drawing Sheets

(56) References Cited

U.S. PATENT DOCUMENTS

| | | | |
|---|---|---|---|
| 4,906,166 A * | 3/1990 | Seidel | F04C 15/0049 |
| | | | 417/414 |
| 6,431,050 B1 | 8/2002 | Hausman | |
| 7,866,286 B2 | 1/2011 | Sun | |
| 8,051,764 B2 | 11/2011 | Jacobsen | |
| 8,201,473 B2 | 6/2012 | Knoll | |
| 8,700,215 B2 | 4/2014 | Komatsu | |
| 8,956,421 B2 * | 2/2015 | Streeter | A61F 2/76 |
| | | | 623/57 |
| 11,434,936 B2 * | 9/2022 | Ziemens | F15B 11/163 |
| 11,746,801 B2 * | 9/2023 | Sahlman | F15B 1/265 |
| | | | 60/477 |
| 12,025,159 B2 * | 7/2024 | Tian | F15B 20/004 |
| 2017/0328381 A1 * | 11/2017 | Goto | F15B 13/06 |
| 2020/0300275 A1 | 9/2020 | Biwersi | |
| 2022/0307523 A1 | 9/2022 | Hill et al. | |
| 2024/0351225 A1 * | 10/2024 | Asada | B25J 9/06 |

OTHER PUBLICATIONS

U.S. Appl. No. 17/689,352, Final Office Action Mailed Dec. 2, 2022, 20 pp.

* cited by examiner

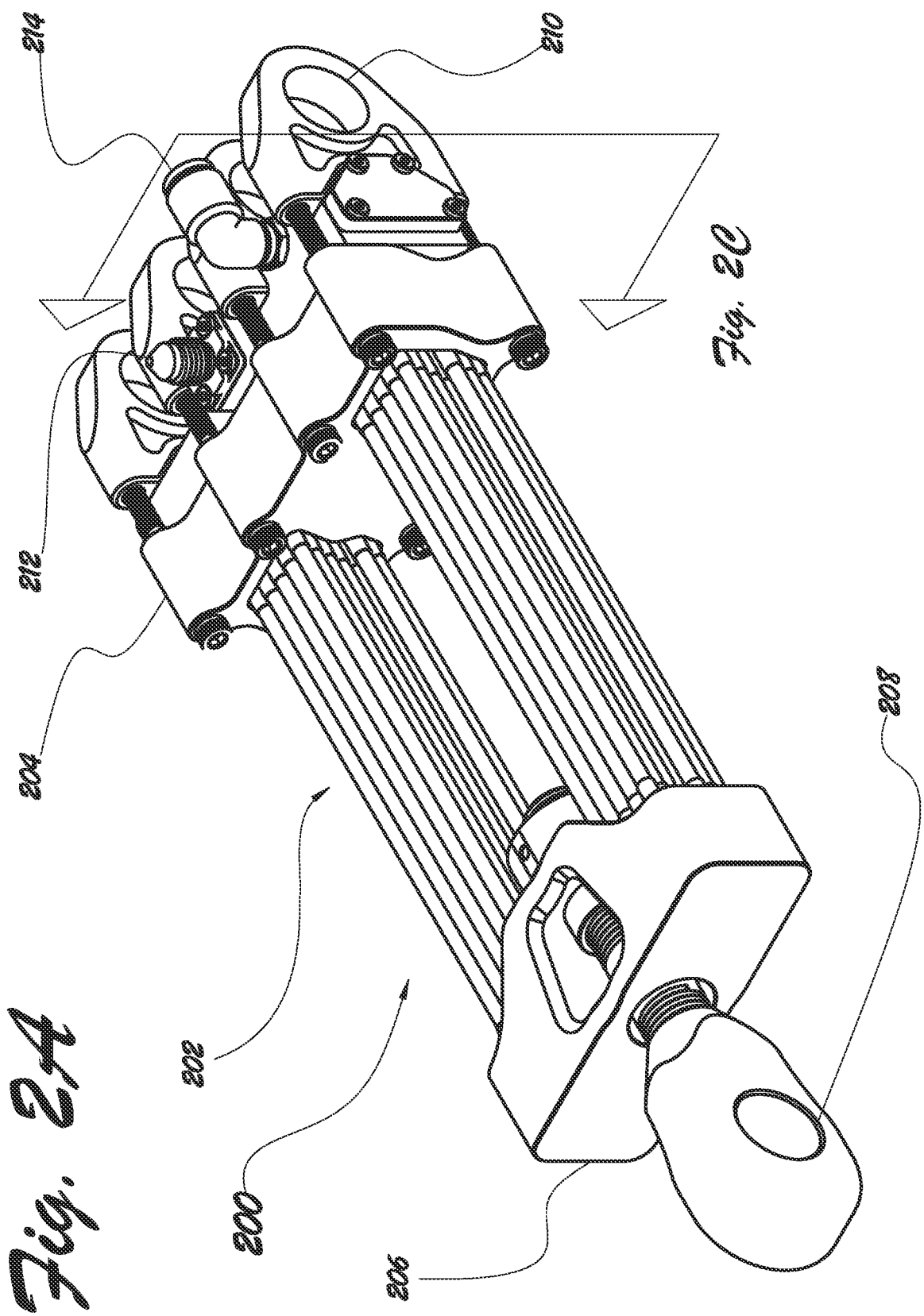

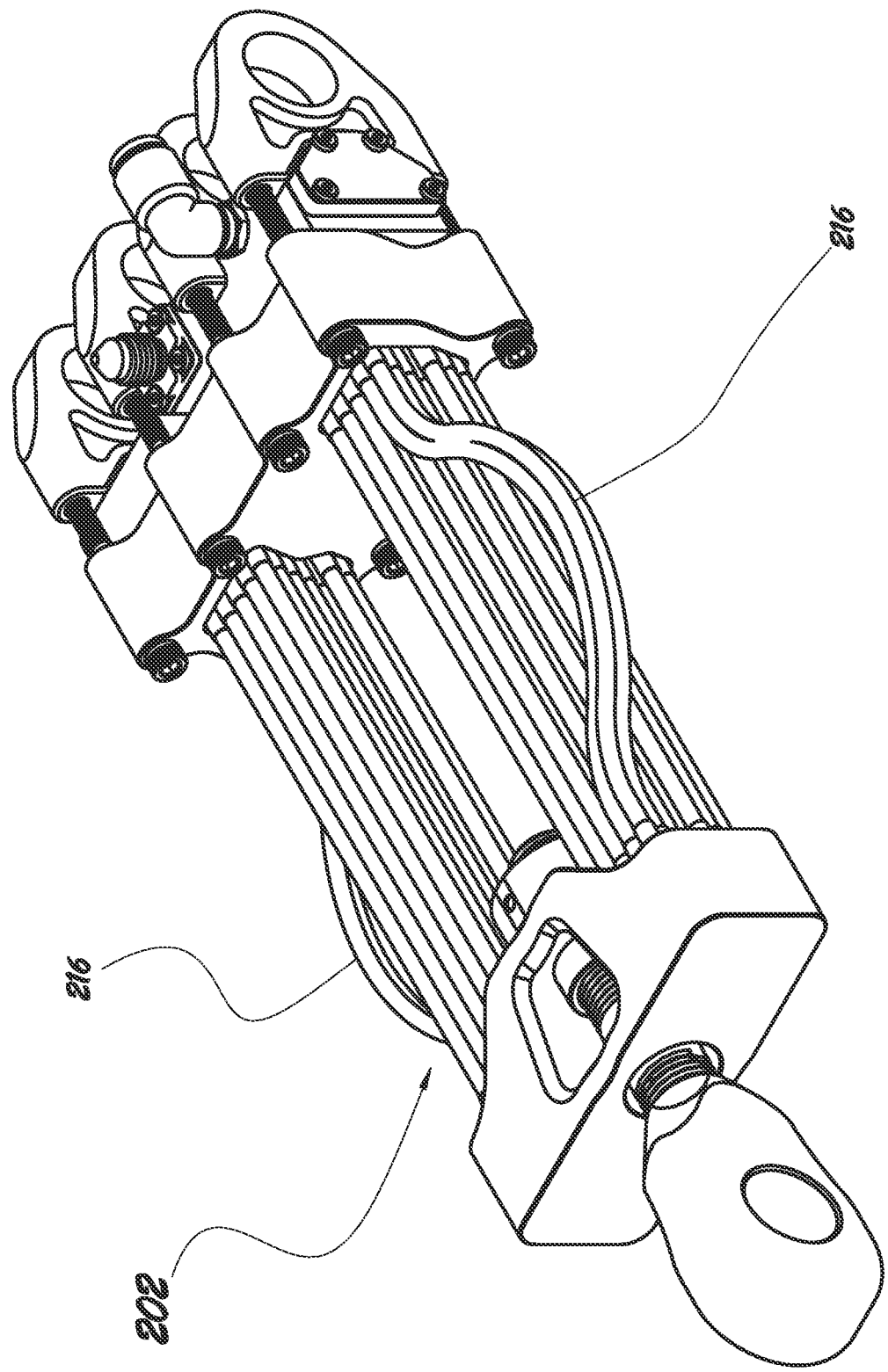

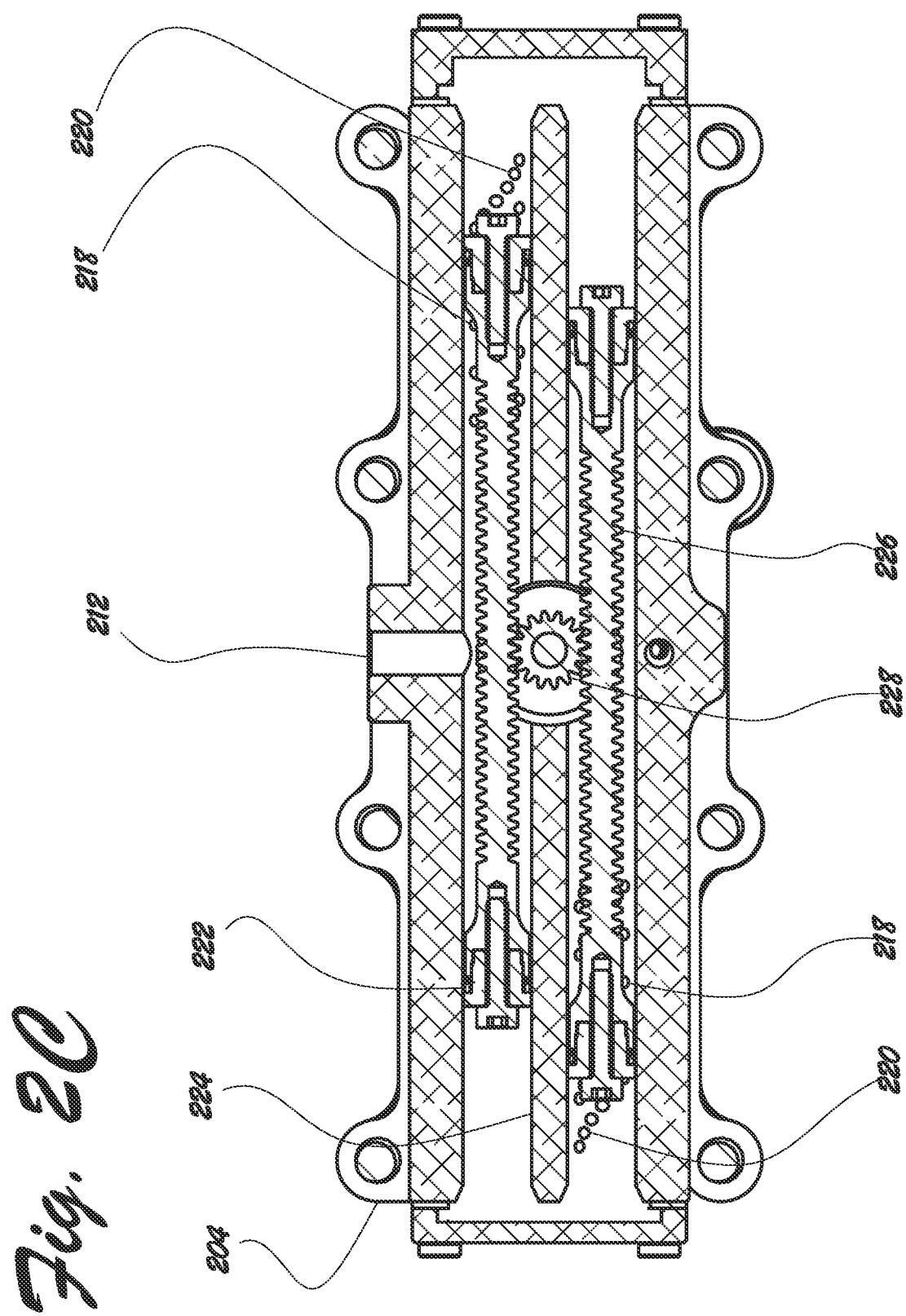

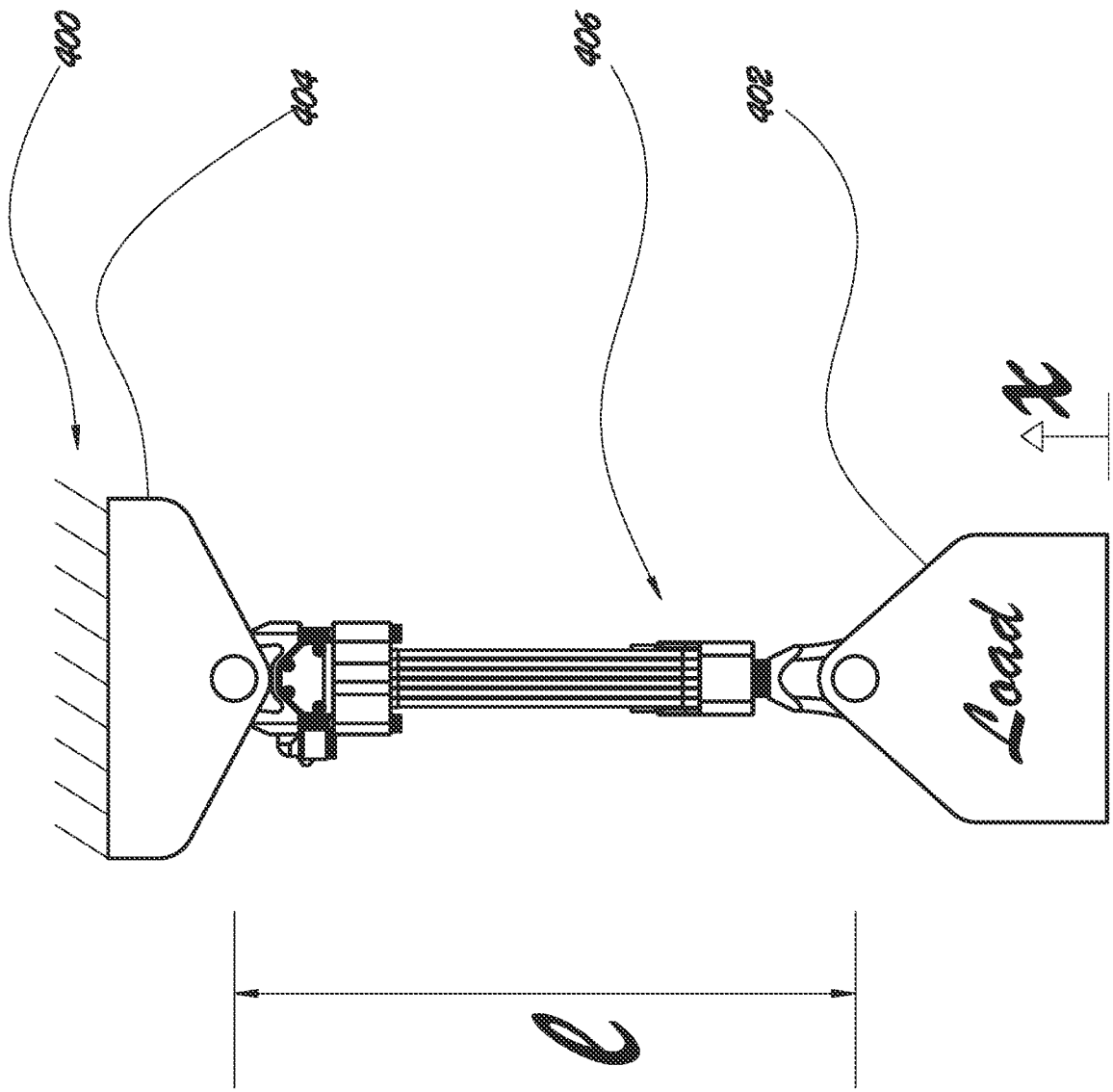

*Fig. 8*
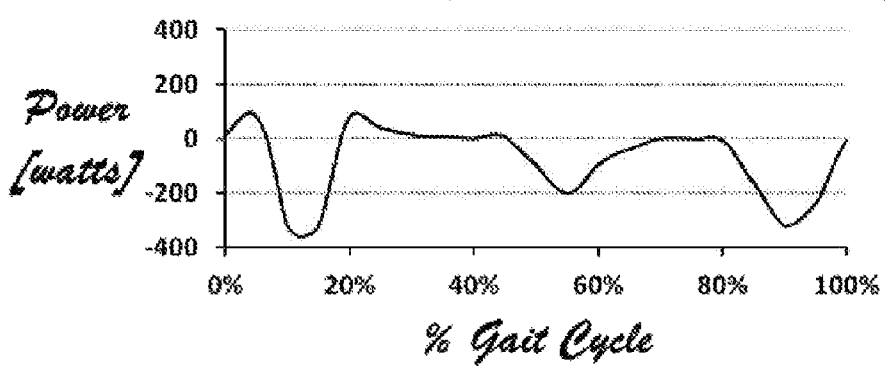
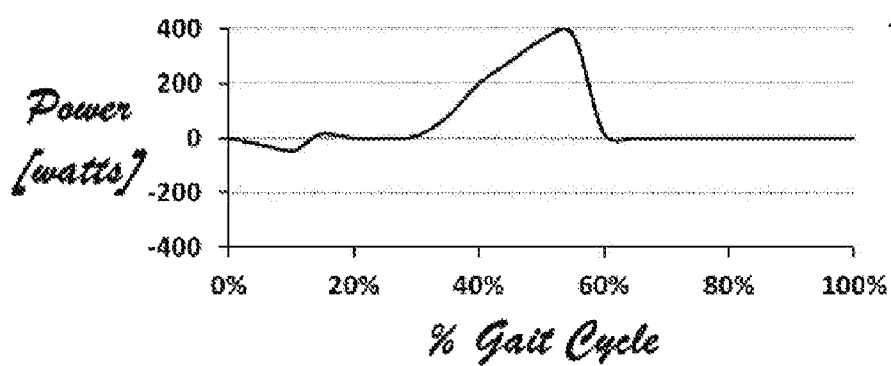
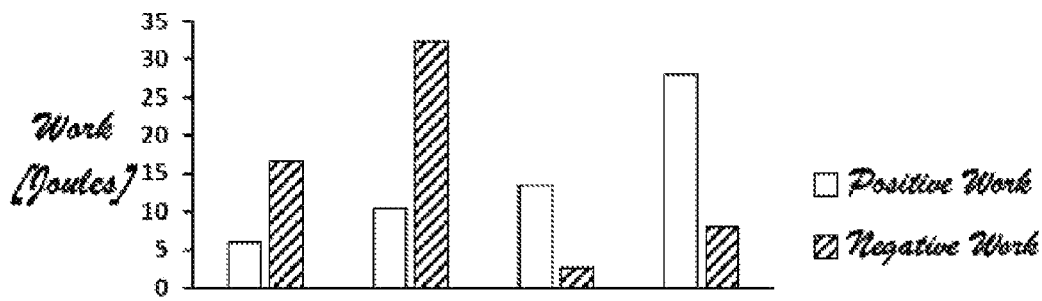

DYNAMIC RECRUITMENT MODULATION IN SYSTEMS UTILIZING VARIABLE RECRUITMENT

RELATED APPLICATIONS

This application claims priority to and is a Continuation-in-Part of U.S. Utility application Ser. No. 17/689,352, filed on Mar. 8, 2022, entitled "VARIABLE RECRUITMENT ACTUATOR SYSTEMS AND RELATED METHODS," which claims priority from and benefit of U.S. Provisional Application Ser. No. 63/165,411, filed on Mar. 24, 2021, entitled "VARIABLE RECRUITMENT ACTUATOR AND METHOD," each of which is hereby incorporated by reference in its entirety for all purposes.

TECHNICAL FIELD

The present disclosure relates to hydraulically driven variable recruitment McKibben muscles. More particularly, the present disclosure relates to a design for and method of allowing inactive McKibben muscles to be recruited in a stable and efficient manner. The present disclosure additionally relates to hydraulic regenerative energy harvesting in a system utilizing one or more variable recruitment actuators in conjunction with one or more hydraulic energy storage elements, allowing for energy savings in applications requiring controlled eccentric motion, such as powered prosthetic and orthotic devices and legged mobile robots.

BRIEF DESCRIPTION OF THE DRAWINGS

Some embodiments of the present disclosure are illustrated as examples and are not limited by figures of the following drawings, in which like references may indicate similar elements and in which:

FIG. 2A depicts a perspective view of an embodiment of a variable recruitment actuator mechanism consistent with embodiments of the present disclosure.

FIG. 2B depicts a buckling behavior of a subset of inactive McKibben muscles of the variable recruitment actuator illustrated in FIG. 2A and consistent with embodiments of the present disclosure.

FIG. 2C depicts a cross-section view of the variable recruitment actuator of FIG. 2A and depicts a method of controlling which subset of a plurality of actuators are active, and which subset of a plurality of actuators are inactive consistent with embodiments of the present disclosure.

FIG. 3B depicts a second simplified hydraulic circuit that utilizes a high-pressure accumulator to store hydraulic energy consistent with embodiments of the present disclosure.

FIG. 4 depicts a perspective view of an actuation system consistent with embodiments of the present disclosure.

FIG. 8 depicts plots of the power and work produced by a knee joint and an ankle joint during a typical human walking and running gait cycle consistent with embodiments of the present disclosure.

DETAILED DESCRIPTION

Figure 1A:
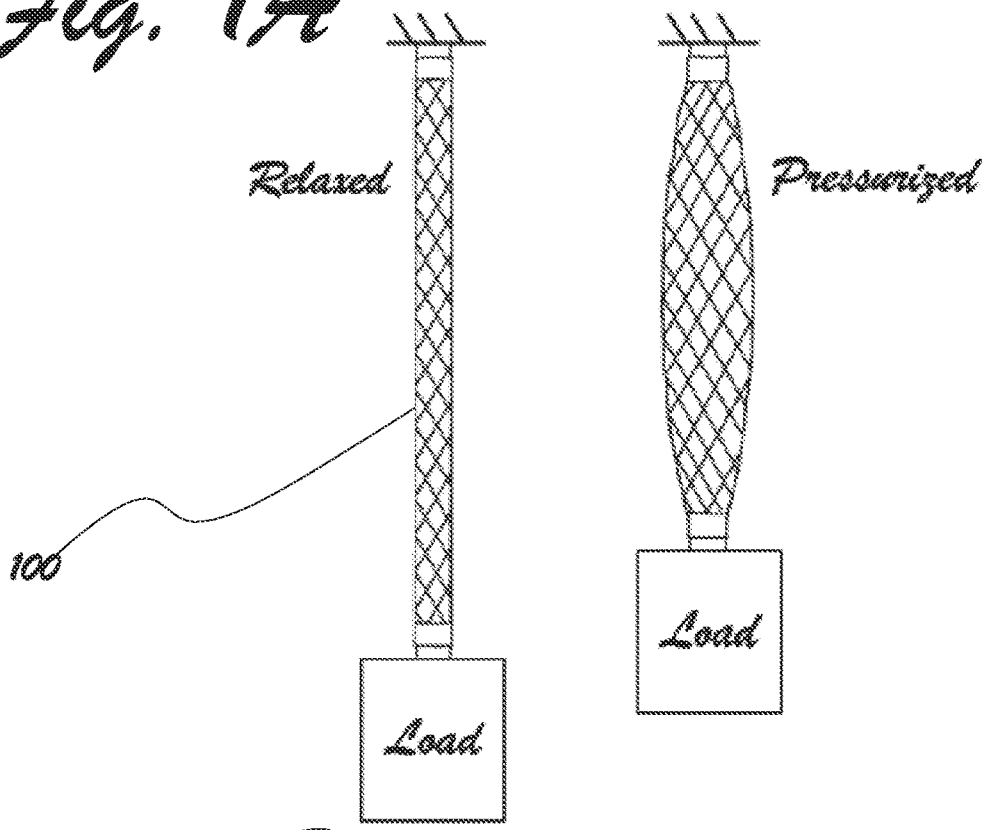
FIG. 1A depicts a McKibben muscle in relaxed and pressurized configurations, and which may be used in various embodiments consistent with the present disclosure.

Variable recruitment actuators utilizing McKibben muscles may have improved efficiency and controllability when compared to standard, single-motor unit fluidic actuators. By modulating the number of individual McKibben muscles used to power a load, the overall performance of a hydraulic system can be improved via the reduction of throttling losses, especially when a plurality of variable recruitment actuators are powered by a single central hydraulic pump coupled to a motor.

One potential problem with variable-recruitment actuators is the potential for unsteady and inefficient motion provided when recruitment is modulated dynamically, as may be the case in many applications. Such inefficient and unsteady motion is due to the natural buckling behavior of McKibben muscles. Instead of drawing in fluid when contracted by external forces, McKibben muscles tend to buckle. Therefore, when an inactive McKibben muscle is activated while a number of active muscles are contracting, fluid rushes into the buckled, non-contracted muscle. This may cause a lagging motion and a sharp decrease in the hydraulic system's efficiency when hydraulic energy storage devices such as accumulators are utilized.

Various embodiments of the present disclosure may reduce or prevent unsteady motion and/or inefficiencies caused by the dynamic activation of dormant fibers through the use of a hydraulic circuit and a variable recruitment valve. Such circuits may allow for efficient and controllable hydraulic regenerative energy harvesting in applications where both controlled concentric and eccentric movements are required.

Hydraulic systems consistent with the present disclosure may be utilized in a variety of applications, such as the control of a prosthesis, robot, or exoskeleton. Applications that require cyclic concentric and eccentric movements (such as the knee joint of a prosthetic device) may benefit from the hydraulic regenerative energy harvesting disclosed in the present application, as energy may be harvested from the eccentric movements and used to help provide concentric motion in the future. Additionally, such systems may provide stable, efficient actuation in aircraft, heavy equipment, and in a variety of additional industrial applications.

The terminology used herein is for the purpose of describing particular embodiments only and is not intended to be limiting. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

Various techniques and steps are disclosed in connection with various embodiments. Each of these has individual benefits and each can also be used in conjunction with one or more, or in some cases all, of the other disclosed techniques. Accordingly, for the sake of clarity, this description does not repeat every possible combination of individual steps. Nevertheless, the specification and claims should be read with the understanding that such combinations are within the scope of the present disclosure.

The present disclosure is to be considered as an exemplification of specific embodiments, and is not intended to limit the claims as understood by one of skill in the art.

FIG. 1A depicts a McKibben muscle, which is the form of actuator used for individual actuators in various embodiments consistent with the present disclosure. The McKibben muscle actuator 100 may expand radially and may contract axially when pressurized. A plurality of McKibben muscles, similar to the McKibben muscle shown in FIG. 1A, may be well suited for use in a variable recruitment actuator, as they may be lightweight, may not require the use of dynamic rod or piston seals, and may be readily manufacturable even at high length-to-diameter ratios.

Figure 1B:
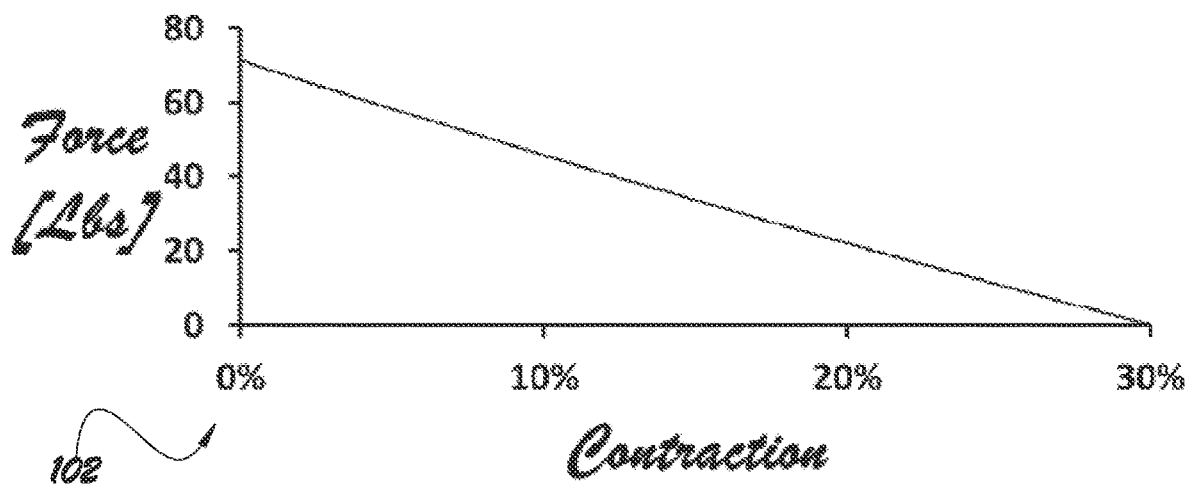
FIG. 1B depicts a plot of contraction versus force for a McKibben muscle consistent with embodiments of the present disclosure.

FIG. 1B depicts a plot 102 of contraction versus force for a McKibben muscle consistent with embodiments of the present disclosure. Plot 102 may depict the force provided by a typical McKibben muscle relative to the McKibben muscle's contraction at a constant pressure. While the theoretical relationship between a McKibben muscle's force and contraction may be non-linear, a linear approximation may provide reasonable accuracy when fit to empirically gathered data, especially in McKibben muscles utilizing a relatively tight braided sleeve that may limit the maximum contraction of the muscles to approximately twenty-five (25) to thirty (30) percent. Additionally, the force provided by a McKibben muscle may be proportional to the pressure of the fluid supplied to its inlet.

FIG. 2A depicts a perspective view of an embodiment of a variable recruitment actuator mechanism 200 consistent with embodiments of the present disclosure. The variable recruitment actuator mechanism 200 may include a plurality of actuators 202 affixed to a first housing 204 and a second housing 206. Each of the plurality of actuators 202 may be McKibben muscle actuators. Second housing 206 may connect each of the plurality of actuators 202 to a shared load via a lower eyelet 208. First housing 204 may connect each of the plurality of actuators 202 to a shared mechanical reference via a plurality of upper eyelets 210. First housing 204 additionally may contain a plurality of fluidic valve components utilized to provide variable recruitment. The positions of these internal components may determine which of the actuators within the plurality of actuators are active and which of the actuators are inactive.

Variable recruitment actuator mechanism 200 may include a high-pressure fluid port 212 to receive a high-pressure fluid. In some embodiments, the high-pressure fluid may have a pressure of approximately 1000 to 5000 pounds per square inch (PSI). The high-pressure fluid may be selectively provided to activate a first subset of the plurality of actuators 202. A lower-pressure fluid port 214 may receive a fluid at a lower pressure. For example, the lower-pressure fluid may have a pressure of approximately 30 to 300 PSI. In some embodiments, the lower-pressure fluid may comprise a range that prevents buckling of McKibben muscles. The lower-pressure fluid may be provided to a second subset of the plurality of actuators 202 that are not activated by the high-pressure fluid.

FIG. 2B depicts the buckling behavior of a subset of inactive McKibben muscles of the variable recruitment actuator mechanism 200 illustrated in FIG. 2A and consistent with embodiments of the present disclosure. While variable recruitment actuators are capable of providing improved actuation efficiency in certain applications, dynamic adjustments to the recruitment level of a variable recruitment actuator utilizing McKibben muscles may cause both unsteady motion and inefficiencies. This may be due to the natural buckling behavior of McKibben muscles as depicted in FIG. 2B. When external compressive forces are applied to the inactive McKibben muscles, the inactive McKibben muscle actuators 216 may not tend to contract but may instead tend to buckle. Because the actuators have buckled, they may not draw in additional fluid from the low-pressure second fluid port 214 regardless of whether the variable recruitment actuator mechanism 200 contracts further.

If previously inactive McKibben muscle actuators 216 are recruited, they may first be filled with a significant amount of fluid before providing a contractile force. This may cause two primary problems: the motion of the variable recruitment actuator mechanism 200 may become noticeably perturbed, and large amounts of hydraulic energy may be wasted in systems utilizing hydraulic energy storage elements such as accumulators.

FIG. 2C depicts a cross-section view of the first housing 204 of the variable recruitment actuator mechanism 200 of FIG. 2A consistent with embodiments of the present disclosure. High-pressure fluid port 212 may supply relatively high-pressure fluid to inlets 218 of a subset of the plurality of actuators 202. Lower-pressure fluid may supply a plurality of inlets 220 with the lower-pressure fluid.

Dynamic hydraulic seals 222 may seal against bores 224 to prevent the high-pressure fluid from leaking to the area containing lower-pressure fluid. Depending on the requirements of a variable recruitment actuator system, the dynamic seals may be replaced with sealless, close-fitting hydraulic spools, that may provide less drag at the expense of significantly greater leakage of high-pressure fluid to the low-pressure area. A central gear 228 may be used to adjust the positions of two gear racks 226, which may adjust the positions of the dynamic hydraulic seals 222 and may determine which of the plurality of actuators 202 are active and which of the plurality of actuators 202 are inactive.

The total contractile force provided by the variable recruitment actuator mechanism 200 may be proportional to the number of individual actuators recruited. For example, if the number of McKibben muscle actuators 216 recruited is doubled while the pressure of the fluid supplied to high-pressure fluid port 212 remains constant, the amount of force provided by the variable recruitment actuator mechanism 200 may also be doubled. Depending on the total desired contractile force from the variable recruitment actuator mechanism 200, the pressure of the hydraulic fluid supplied to high-pressure fluid port 212, and the current percentage contraction of the plurality of actuators 202, an appropriate number of the plurality of actuators 202 may be recruited to provide approximately the total desired contractile force.

The ability to vary the number of individual McKibben muscle actuators 216 recruited to provide a desired force may allow a number of benefits. In the simplest example, when a hydraulic system utilizes a single variable recruitment actuator to provide controlled concentric motion, the variable recruitment actuator may alter its recruitment level to ensure that a pump powering the variable recruitment actuator may operate efficiently, regardless of the loads applied to the actuator. For example, if a hydraulic pump achieves its peak mechanical efficiency when providing a pressure of 1000 PSI, the variable recruitment actuator may alter its recruitment level, based on forces desired, to maintain a system pressure near 1000 PSI. Additionally, in a system utilizing a central hydraulic power unit to power a plurality of variable recruitment actuators, the recruitment levels of each of the variable recruitment actuators may be adjusted to help minimize throttling losses.

A variety of variable recruitment actuator mechanisms are illustrated in U.S. Utility application Ser. No. 17/689,352. As one of skill in the art will appreciate, any of these variable recruitment actuator mechanisms may be utilized in connection with the systems and methods disclosed herein.

Figure 3A:
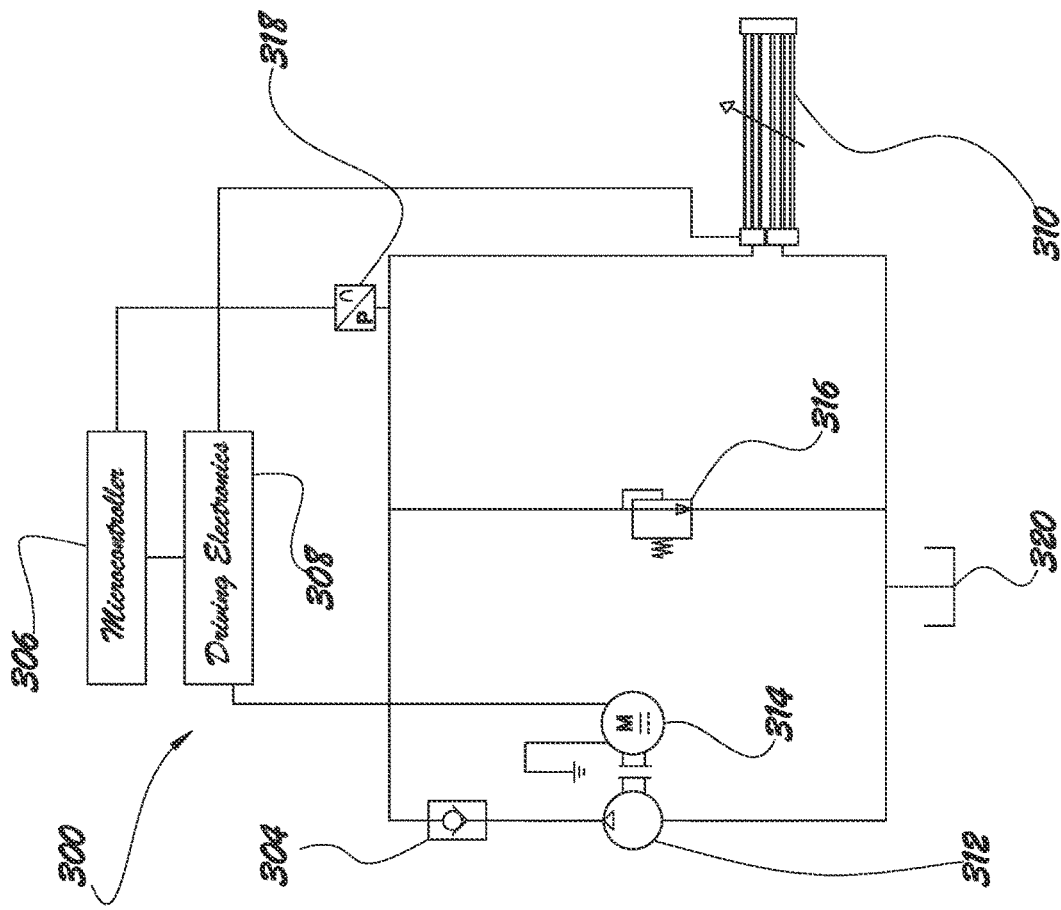
FIG. 3A depicts a first simplified hydraulic circuit utilizing a variable recruitment actuator consistent with embodiments of the present disclosure.

FIG. 3A depicts a first simplified hydraulic circuit 300 utilizing a variable recruitment actuator 310 consistent with embodiments of the present disclosure. The first simplified hydraulic circuit 300 may utilize a coupled pump 312 and motor 314 that may provide fluid power. A check valve 304 may prevent fluid from flowing through pump 312 when pump 312 is inactive. A pressure relief valve 316 may provide over-pressurization relief. A reservoir 320 may provide fluid for use in the first simplified hydraulic circuit 300.

A microcontroller 306 may be in communication with driving electronics 308. A signal from driving electronics 308 may control motor 314. Driving electronics 308 may include, among other things, motor speed controllers, solenoid valve current controllers, etc. A pressure transducer 318 may generate a measurement of the pressure of the working fluid and provide the measurement to microcontroller 306 for use in controlling the first simplified hydraulic circuit 300. Driving electronics 308 may also be in communication with variable recruitment actuator 310. Driving electronics 308 may selectively recruit a subset of a plurality of actuators to control motion of variable recruitment actuator 310. Microcontroller 306 and driving electronics 308 may comprise a control system configured to control first simplified hydraulic circuit 300.

FIG. 3B depicts a second simplified hydraulic circuit 350 that utilizes a high-pressure accumulator 372 to store hydraulic energy consistent with embodiments of the present disclosure. The second simplified hydraulic circuit 350 may utilize a coupled pump 362 and motor 364 that may provide fluid power. A check valve 354 may prevent fluid from flowing through pump 362 when pump 362 is inactive. A pressure relief valve 366 may provide over-pressurization relief. A fluid source 370 may provide fluid for use in the second simplified hydraulic circuit 350.

A microcontroller 356 may be in communication with driving electronics 358. A signal from driving electronics 358 may control pump 362. A pressure transducer 368 may provide pressure data to microcontroller 356 for use in controlling the second simplified hydraulic circuit 350. Driving electronics 358 may also be in communication with a variable recruitment actuator 360. Driving electronics 358 may selectively recruit a subset of a plurality of actuators to control motion of variable recruitment actuator 360.

In contrast to the first simplified hydraulic circuit 300, the second simplified hydraulic circuit 350 includes high-pressure accumulator 372 and directional valve 374. If the directional valve 374 is used to prevent fluid from flowing into the variable recruitment actuator 360, the pump 362 may be used to charge the high-pressure accumulator 372. At a later point in time, if the pump 362 is stopped and the directional valve 374 is opened, allowing fluid to flow into the variable recruitment actuator 360, the high-pressure accumulator 372 may be used to supply pressurized fluid to the variable recruitment actuator 360. Therefore, in contrast to the first simplified hydraulic circuit 300, the second simplified hydraulic circuit 350 may allow the variable recruitment actuator 360 to contract while the pump 362 remains inactive.

FIG. 4 depicts a perspective view of a variable recruitment actuation system 400 consistent with embodiments of the present disclosure. A variable recruitment actuator 406 may be connected to a load 402 and a fixed mechanical reference 404. When the variable recruitment actuator 406 is supplied pressurized fluid, each of a plurality of active McKibben muscles may contract, which may lead to a decrease in length "l" and may cause displacement "x" of the load 402. As active McKibben muscles contract, their contractile force decreases assuming the supplied pressure remains constant. Therefore, as the displacement of the load increases, an increasing number of McKibben muscles must be activated to provide sufficient contractile to apply a desired force. In some embodiments, variable recruitment actuation system 400 may be connected to first simplified hydraulic circuit 300 illustrated in FIG. 3A, second simplified hydraulic circuit 350 illustrated in FIG. 3B, or other hydraulic circuits.

Figure 5B:
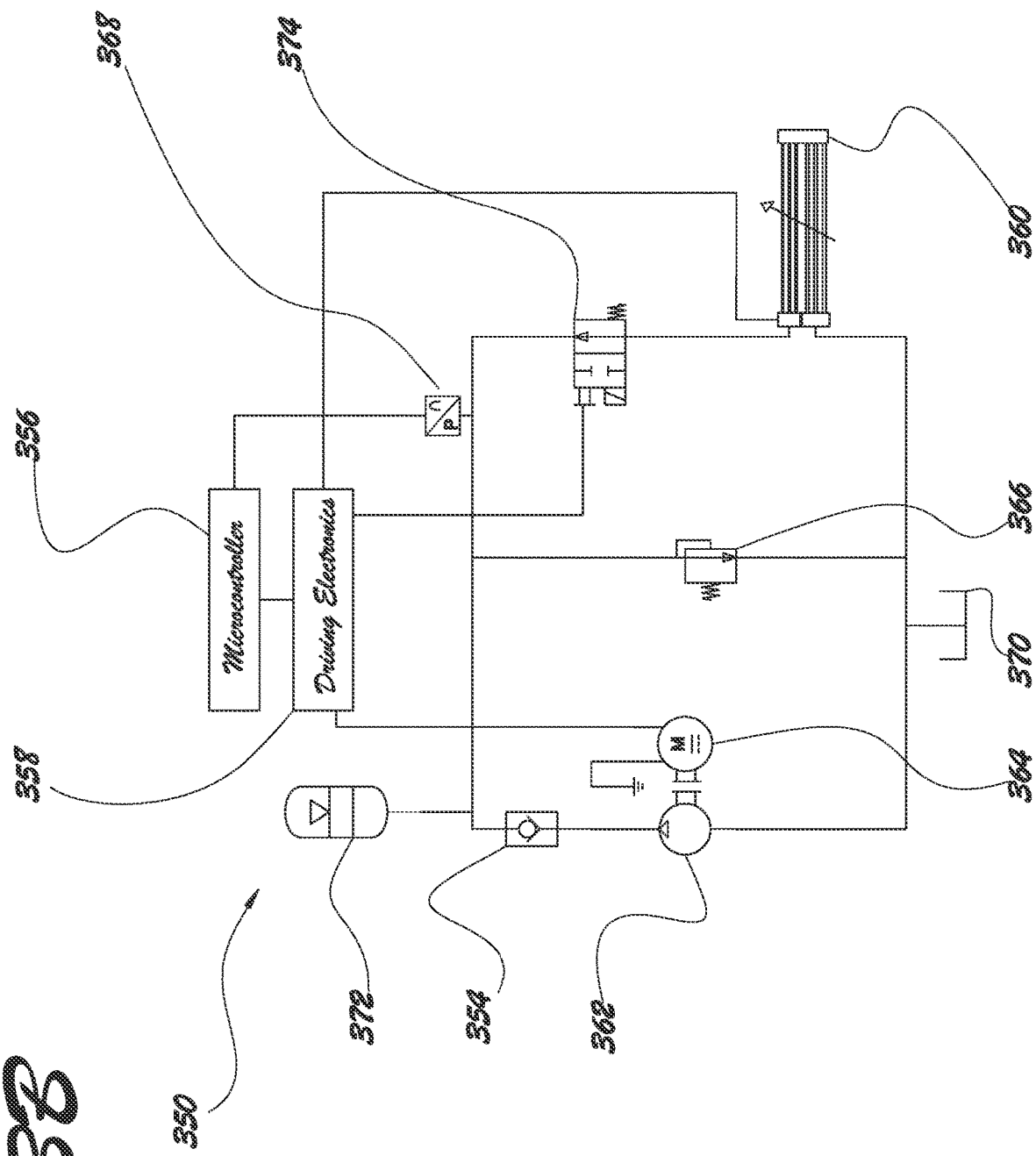
FIG. 5B illustrates a plot of efficiency versus recruitment level consistent with embodiments of the present disclosure.
Figure 5A:
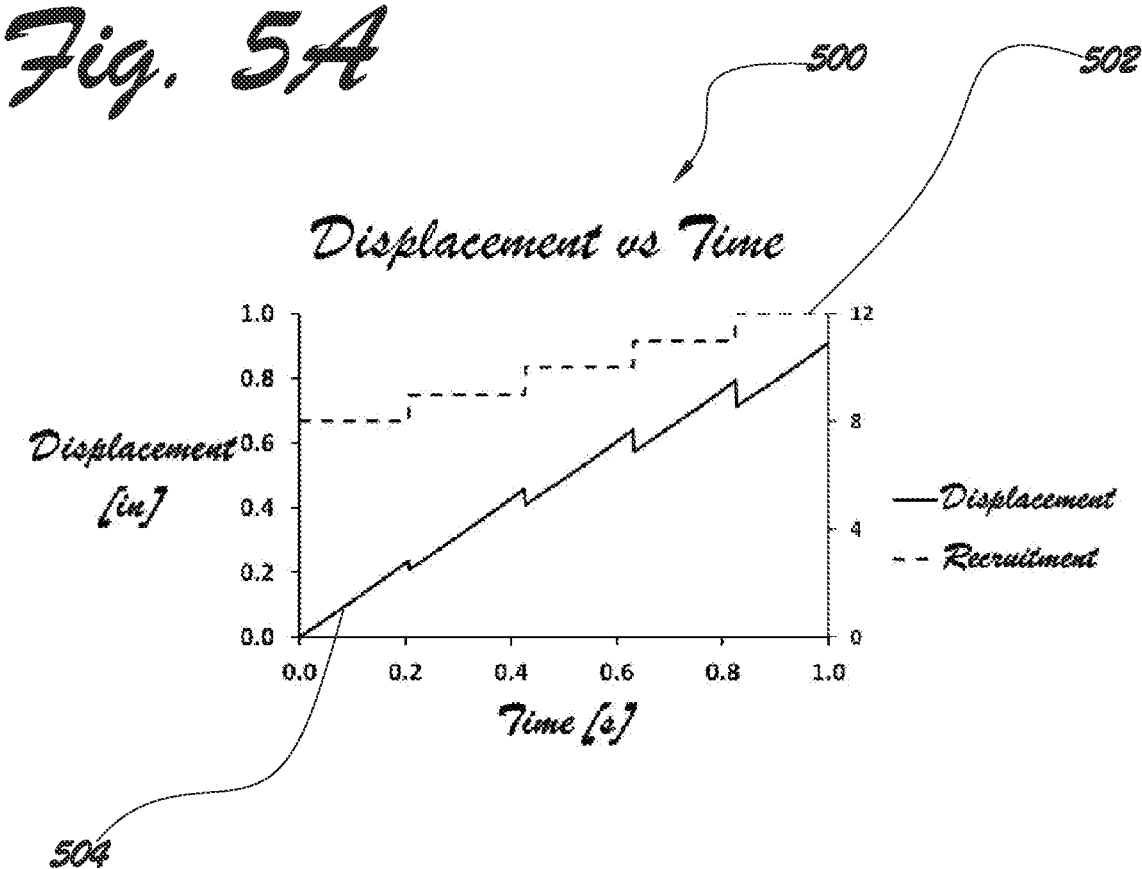
FIG. 5A illustrates a plot over time of a number of actuators and a displacement consistent with embodiments of the present disclosure.
Figure 5B:

FIG. 5A illustrates a plot 500 over time of the recruitment of a number of actuators 502 and a displacement 504 of said actuators consistent with embodiments of the present disclosure. The plot of displacement 504 illustrates unsteady motion that may be caused by the activation of buckled inactive McKibben muscles during concentric movements. Plot 500 may illustrate a scenario in which a flow rate of a pump may be constant and a recruitment level of a variable recruitment actuator may be increased to allow the pump to provide fluid at a near-constant pressure. When the recruitment level of the variable recruitment actuator is increased and a previously inactive, buckled McKibben muscle is filled with fluid, fluid may briefly flow outwards from the previously recruited muscles into the newly recruited muscle. This flow may cause the variable recruitment actuator to briefly elongate as shown by the sharp change in displacement 504. In general, loads with relatively low inertia may display this form of unsteady motion. Smooth and precise control over motion may be preferable to unsteady motion in a variety of applications, such as robotics, powered prosthetics, and powered orthotics.

FIG. 5B illustrates a plot 510 of efficiency versus recruitment level consistent with embodiments of the present disclosure. As shown in plot 510, efficiency decreases as the recruitment level increases. The decrease in efficiency may be caused by pressurized fluid from recruited actuators escaping into actuators being recruited. The energy stored in the pressurized fluid may be lost as fluid initially fills buckled, previously-unrecruited actuators.

Efficiency and/or motion stability may be improved by avoiding the effects of buckled dormant McKibben muscles. In various embodiments, fluid of a relatively low pressure may be supplied to the inactive McKibben muscles to cause the inactive McKibben muscles to contract along with the active McKibben muscles. The inactive McKibben muscles may provide a minimal contribution to the total contractile force of the variable recruitment actuator because the fluid supplied may be at a lower pressure relative to the pressure of the fluid supplied to the recruited McKibben muscles. One of a number of forms of pressurized reservoirs may be used to provide the low-pressure fluid to the inactive McKibben muscles. In various embodiments, the lower-pressure fluid may be provided by a pressurized accumulator acting as a reservoir, or by utilizing a bootstrap reservoir. The hydraulic circuits depicted in FIGS. 6A-6B may both utilize a pressurized reservoir, which may prevent the buckling behavior of McKibben muscles and the associated inefficiencies.

Figure 6B:
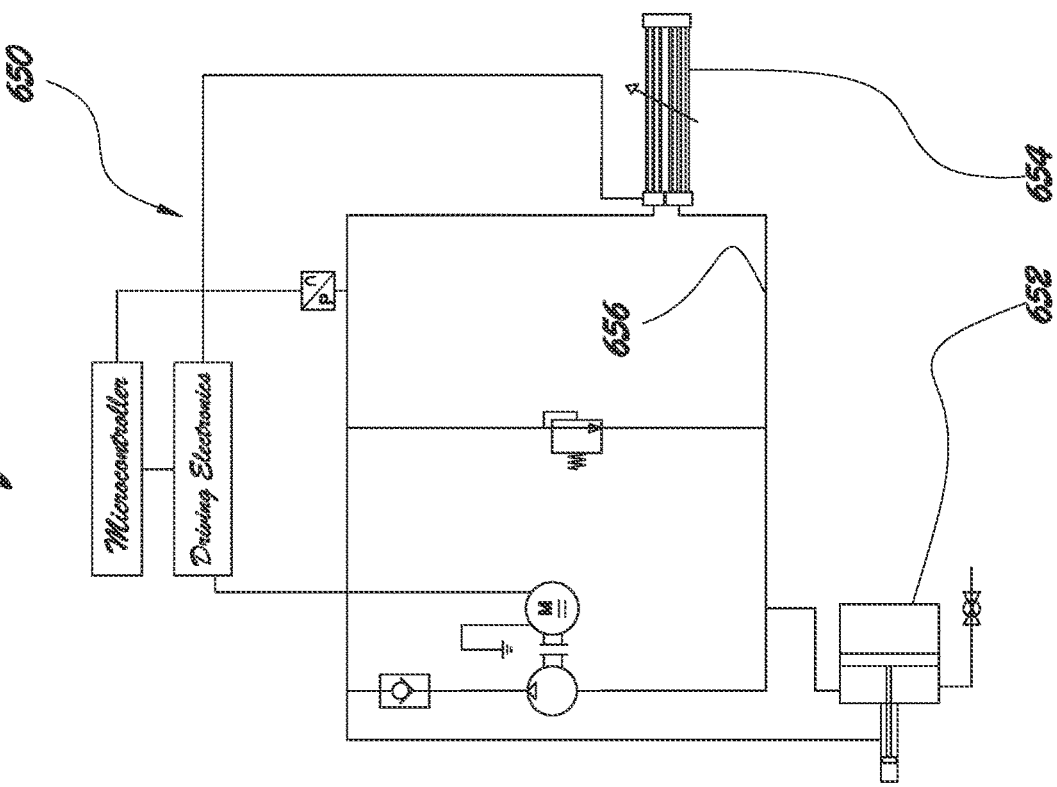
FIG. 6B depicts a second hydraulic circuit configured for use in connection with the variable recruitment actuator and to provide improved stability and efficiency by providing a bootstrap reservoir to provide low-pressure fluid to inactive actuators consistent with embodiments of the present disclosure.
Figure 6A:
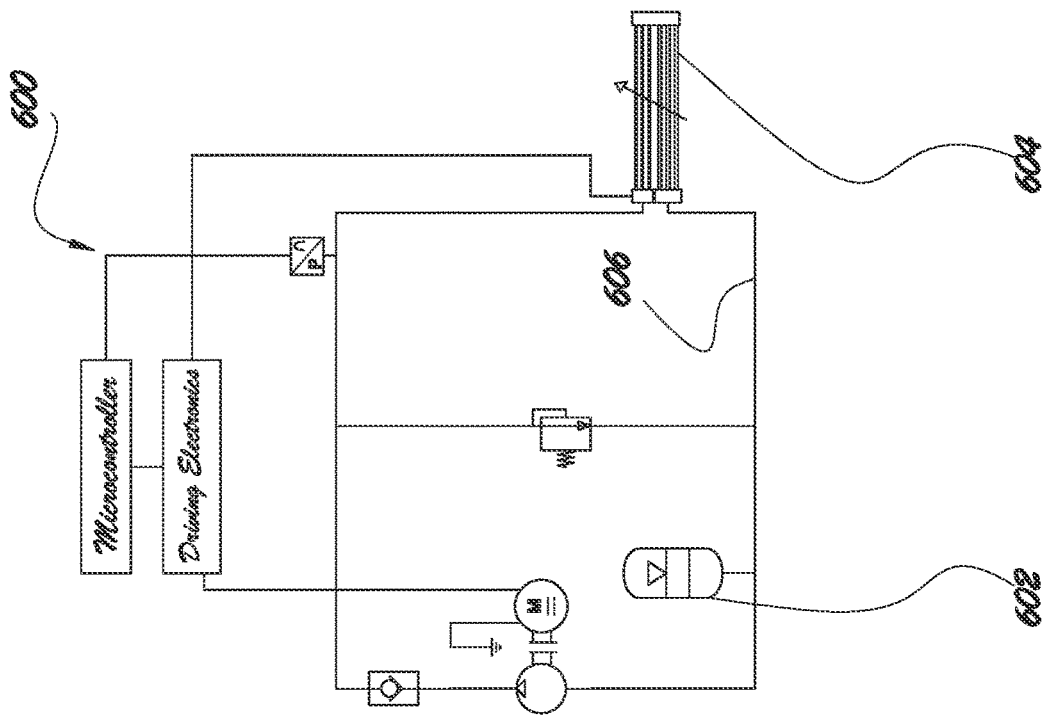
FIG. 6A depicts a first hydraulic circuit configured for use in connection with a variable recruitment actuator and to provide improved stability and efficiency by providing a relatively low-pressure fluid to inactive actuators consistent with embodiments of the present disclosure.

FIG. 6A depicts a first hydraulic circuit 600 configured for use in connection with a variable recruitment actuator 604 and to provide improved stability and efficiency by providing a relatively low-pressure fluid to inactive actuators consistent with embodiments of the present disclosure. In first hydraulic circuit 600, a low-pressure accumulator 602 may be used to increase a reservoir pressure of first hydraulic circuit 600. In some embodiments, low-pressure accumulator 602 may maintain a pressure of approximately 30-300 PSI. Low-pressure accumulator 602 may have a lower-pressure fluid connection 606 to the variable recruitment actuator 604. Lower-pressure fluid connection 606 may be provided to inactive McKibben muscle fibers through a secondary fluid port. The lower-pressure fluid provided by lower-pressure fluid connection 606 may prevent buckling of dormant McKibben muscles. In one specific embodiment, low-pressure accumulator 602 may be sized and pressurized such that it may maintain a high enough pressure to contract a McKibben muscle at its lowest fluid capacity. Low-pressure accumulator 602 may operate as a low-pressure fluid source in first hydraulic circuit 600.

FIG. 6B depicts a second hydraulic circuit 650 configured for use in connection with a variable recruitment actuator 654 and to provide improved stability and efficiency by providing a bootstrap reservoir 652 to provide low-pressure fluid to inactive actuators consistent with embodiments of the present disclosure. Because the pressure of the bootstrap reservoir may be proportional to the pressure provided by the system's pump, the bootstrap reservoir may be designed such that the reservoir pressure is high enough pressure to completely contract a McKibben muscle at the system's lowest operational pressure. Bootstrap reservoir 652 may maintain a minimum pressure within second hydraulic circuit 650. In some embodiments, bootstrap reservoir 652 may maintain a minimum pressure between approximately 30 and 300 PSI.

As working fluid cycles through second hydraulic circuit 650, high-pressure fluid used to selectively recruit a subset of the actuators that comprise variable recruitment actuator 654 may be directed to bootstrap reservoir 652. The working fluid that escapes from the subset of recruited actuators retains at least a portion of its hydraulic energy, and this energy may be utilized to pressurize un-recruited actuators in variable recruitment actuator 654 to reduce unsteady motion and/or to reduce the energy used to re-pressurize the inactive actuators. Bootstrap reservoir 652 may operate as a low-pressure fluid source.

Figure 7:
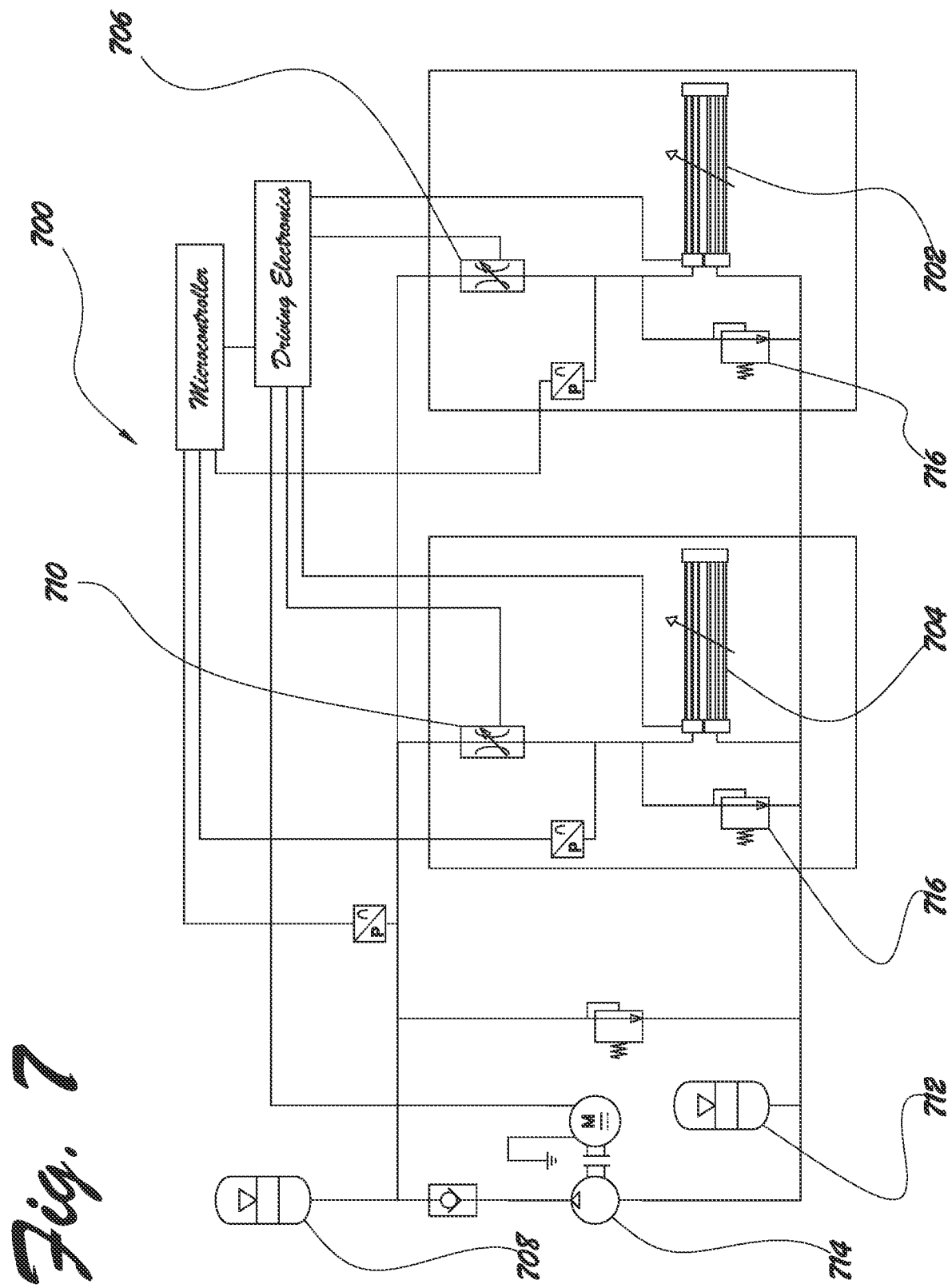
FIG. 7 depicts a design of a hydraulic circuit configured to provide hydraulic regenerative energy harvesting via variable recruitment consistent with embodiments of the present disclosure.

FIG. 7 depicts a design of a hydraulic circuit 700 capable of providing hydraulic regenerative energy harvesting via variable recruitment consistent with embodiments of the present disclosure. A first variable recruitment actuator 702 and a second variable recruitment actuator 704, a low-pressure accumulator 712, and a high-pressure accumulator 708 is depicted. Whenever either of the variable recruitment actuators 702, 704 is utilized to provide controlled eccentric motion, the recruitment level of the variable recruitment actuator 702, 704 providing said controlled eccentric motion may be dynamically adjusted to provide sufficient pressure to charge high-pressure accumulator 708, which may allow the variable recruitment actuator 702, 704 to act as a linear motion analog to a variable displacement pump whenever eccentric motion is required. At a later point in time, the energy stored within accumulator 708 may be used to power either of variable recruitment actuators 702 and 704, providing controlled concentric motion and reducing the total energy consumed by the system to provide motion over time.

Low-pressure accumulator 712 may receive working fluid used to recruit a subset of the variable recruitment actuators 702, 704. Low-pressure accumulator 712 may receive pressurized fluid released from recruited variable recruitment actuators 702, 704, and this working fluid may be used to pressurize unrecruited actuators. By pressurizing unrecruited actuators, hydraulic circuit 700 may reduce or avoid unsteady motion that may be caused by the activation of buckled inactive McKibben muscles during concentric movements.

Adjustments to the pressure within first variable recruitment actuator 702 may be provided using a first throttling valve 706. Adjustments to the pressure within second variable recruitment actuator 704 may be provided using a second throttling valve 710. First throttling valve 706 and second throttling valve 710 may be disposed between the high-pressure accumulator 708 and first variable recruitment actuator 702 and second variable recruitment actuator 704. First throttling valve 706 and second throttling valve 710 may selectively reduce the pressure of the working fluid based on signals from driving electronics. A control system may comprise the driving electronics and the microcontroller.

When providing concentric movements, first throttling valve 706 and second throttling valve 710 may decrease the pressure of the fluid provided by the high-pressure accumulator 708 and pump 714. When providing eccentric movements, first throttling valve 706 and second throttling valve 710 may slightly increase the pressure of an actuator beyond the pressure of the high-pressure accumulator 708. To prevent over pressurization of hydraulic circuit 700, a first relief valve 714 and a second relief valve 716 may be provided. First relief valve 714 and second relief valve 716 may comprise spring-based seals. Pressure exceeding a threshold may compress the spring-based seals and reduce the pressure. Once the excess pressure is relieved, the spring-based seals close. Hydraulic circuit 700 may be utilized in a variety of applications, including prosthetics, orthotics, mobile robotics, or any other application that may provide significant hydraulic regenerative energy harvesting due to the need for controlled eccentric motion.

FIG. 8 depicts plots 800, 802, 804 of the power and work produced by a knee joint and an ankle joint, during a typical human walking and running gait cycle. Plot 800 shows knee power during a gait cycle, and plot 802 shows ankle power during a gait cycle. Plot 804 shows the work performed per stride by a knee joint and an ankle joint while walking and running. A hydraulic regenerative energy harvesting system may take advantage of the energy expenditure of a typical human's lower body joints while walking and running.

Various embodiments consistent with the present disclosure may provide hydraulic regenerative energy harvesting in a system requiring both eccentric and concentric actuation consistent with embodiments of the present disclosure. In the human gait, the knee joint may provide primarily eccentric motion, which may provide "negative" work in the sense that the product of the knee joint's velocity and applied torque may be negative as displayed by knee power chart, as shown in plots 800 and 804. In contrast, the ankle joint may provide primarily concentric motion and may require a net input of work as displayed by plot 802 and 804. Therefore, in a powered prosthetic or orthotic device, it may be preferable to capture the energy provided by the negative work of the knee joint and utilize the energy to provide concentric motion of both the knee and ankle joints of the device, which may allow the size of the system's hydraulic power unit, thermal dissipation components, and batteries to be significantly reduced.

Figure 9:
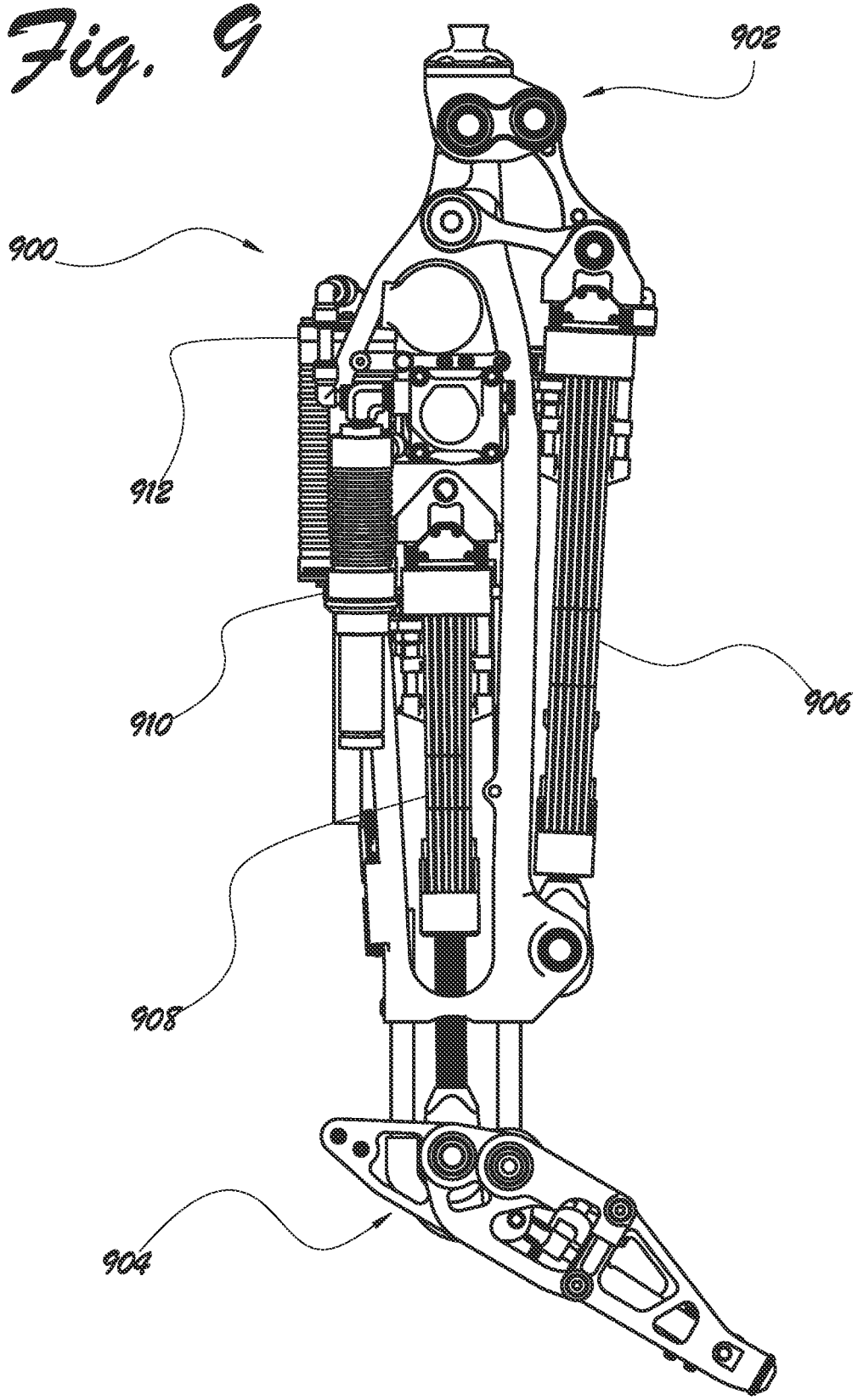
FIG. 9 depicts a prosthetic device comprising a plurality of variable actuators that may utilize energy captured from the controlled eccentric motion of a knee joint to provide concentric motion of an ankle joint consistent with embodiments of the present disclosure.

FIG. 9 depicts a prosthetic device 900 comprising a plurality of variable actuators that may utilize energy captured from the controlled eccentric motion of a knee joint 902 to provide concentric motion of an ankle joint 904 consistent with embodiments of the present disclosure. A first variable recruitment actuator 906 may charge a high-pressure accumulator 910 primarily during periods of a gait cycle that generate negative power. As shown in plot 800 of FIG. 8, negative power from a knee joint is generated during a gait cycle during the period of 8% to 20%, 45% to 70%, and 80% to 100% percent. High-pressure accumulator 910 may then use this energy to provide concentric motion of first variable recruitment actuator 906 and/or the concentric motion of a second variable recruitment actuator 908. The use of high-pressure accumulator 910 to store hydraulic regenerative energy may reduce the energy requirements of prosthetic device 900.

A lower-pressure accumulator 912 may also be provided. Lower-pressure accumulator 912 may provide fluid to unrecruited/inactive McKibben muscle fibers to prevent buckling. Avoiding buckling of inactive McKibben muscle fibers may improve the efficiency of the prosthetic device and may provide more precise control over the motion of prosthetic device 900. In various embodiments, prosthetic device 900 may comprise hydraulic circuit 700, as illustrated in FIG. 7.

Figure 10:
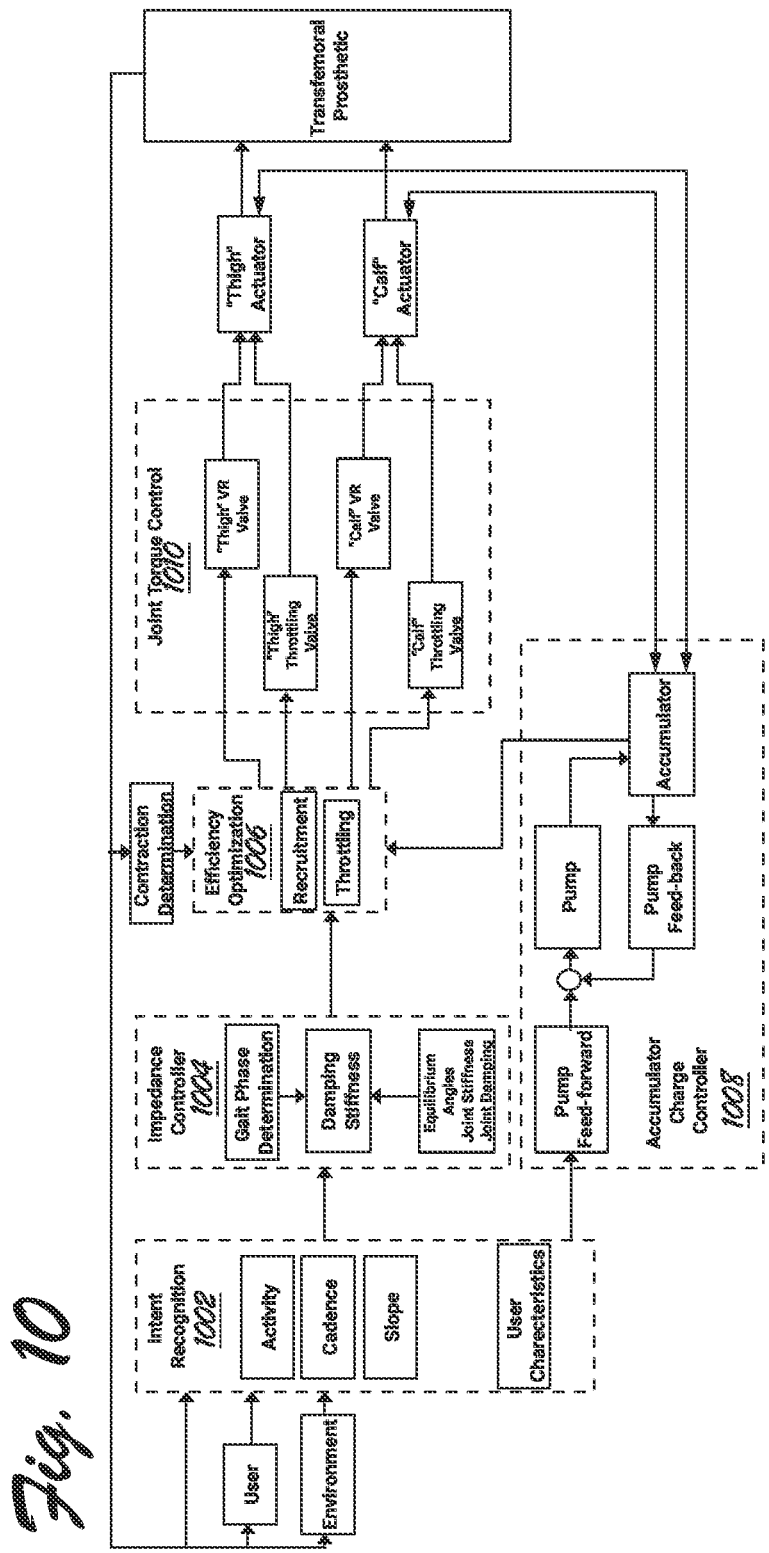
FIG. 10 depicts a block diagram of an example of a control system for a variable recruitment actuator consistent with embodiments of the present disclosure.

FIG. 10 depicts a block diagram of an example of a control system 1000 for a variable recruitment actuator consistent with embodiments of the present disclosure. A block diagram similar to the one shown in FIG. 10 may additionally be useful in a variety of applications, including alternate types of powered prosthetics and orthotic devices, mobile robotics, and other applications.

An intent-recognition controller 1002 may determine a desired activity of a device it controls, the cadence of said activity, and the presence of any slopes. An impedance controller 1004 may determine desired torque outputs of each of the device's joints per the input from the intent-recognition controller 1002. A number of subsequent controllers may then determine how the system may most efficiently provide the desired torque outputs. An efficiency optimization controller 1006 may determine the ideal combination of each actuator's recruitment level and throttling to provide a desired torque output based on the hydromechanical system's pressure and the current contractions of each of the variable recruitment actuators. An accumulator charge controller 1008 may determine the flow rate of the hydraulic system's pump required to maintain the charge of the accumulator. A system comprising control system 1000 may also comprise a high-pressure accumulator sized such that a pump may operate at a near steady, relatively low-power output state, which may minimize the generation of noise within the device. A joint torque control system 1010 may be used to adjust the actual recruitment levels and the actual throttling applied to each of the actuators based on the ideal combinations of recruitment levels and throttling for each of the actuators and any potential limitations of the hydromechanical system. Joint torque control system 1010 may communicate with motor speed and/or position controllers, solenoid current controllers, or any other controllers that may be used to adjust recruitment levels and throttling in the hydromechanical system.

While specific embodiments and applications of the disclosure have been illustrated and described, it is to be understood that the disclosure is not limited to the precise configurations and components disclosed herein. Accordingly, many changes may be made to the details of the above-described embodiments without departing from the underlying principles of this disclosure. The scope of the present disclosure should, therefore, be determined only by the following claims.

What is claimed is:

1. A variable recruitment actuator system, comprising:
 a high-pressure fluid source to provide a working fluid at a first pressure;
 a lower-pressure fluid source to provide the working fluid at a second pressure;
 a plurality of actuators;
 a variable recruitment actuator mechanism to:
  selectively recruit a first subset of the plurality of actuators and to pressurize the first subset of the plurality of actuators with the working fluid from the high-pressure fluid source; and
  pressurize a second subset of the plurality of actuators with the working fluid from the lower-pressure fluid source; and
 a control system to control the variable recruitment actuator mechanism to selectively recruit the first subset of the plurality of actuators;
 wherein the second pressure prevents buckling of a Mckibben muscle.

2. The variable recruitment actuator system of claim 1, wherein the second pressure comprises a range between approximately 30 and 300 pounds per square inch.

3. The variable recruitment actuator system of claim 1, further comprising a pressure relief valve in fluid communication with the lower-pressure fluid source and configured to open when the first pressure exceeds a threshold.

4. The variable recruitment actuator system of claim 1, wherein the lower-pressure fluid source comprises a bootstrap reservoir.

5. The variable recruitment actuator system of claim 1, wherein the high-pressure fluid source comprises a high-pressure accumulator to store the working fluid at the first pressure.

6. The variable recruitment actuator system of claim 1, wherein working fluid used to selectively recruit the first subset of the plurality of actuators is directed to the lower-pressure fluid source.

7. The variable recruitment actuator system of claim 1, wherein the variable recruitment actuator system is comprised within a prosthetic device.

8. The variable recruitment actuator system of claim 1, further comprising a throttling valve disposed between the high-pressure fluid source and the plurality of actuators; wherein the control system is further configured to actuate the throttling valve to decrease the first pressure.

9. The variable recruitment actuator system of claim 1, further comprising:
   a pressure transducer to generate a measure of pressure of the working fluid; and
   a hydraulic pump operable to increase the pressure of the working fluid;
   wherein the control system is further configured to selectively activate the pump based on the measure of pressure of the working fluid.

10. A method of controlling a variable recruitment actuator system, comprising:
    providing, using a high-pressure fluid source, a working fluid at a first pressure;
    providing, using a lower-pressure fluid source, the working fluid at a second pressure;
    providing a plurality of actuators;
    selectively recruiting, using a variable recruitment actuator mechanism, a first subset of the plurality of actuators and to pressurize the first subset of the plurality of actuators with the working fluid from the high-pressure fluid source;
    pressurizing, using the variable recruitment actuator mechanism, a second subset of the plurality of actuators with the working fluid from the lower-pressure fluid source; and
    controlling, using a control system, the variable recruitment actuator mechanism to selectively recruit the first subset of the plurality of actuators;
    wherein the second pressure prevents buckling of a Mckibben muscle.

11. The method of claim 10, wherein the second pressure comprises a range between approximately 30 and 300 pounds per square inch.

12. The method of claim 10, further comprising providing a pressure relief valve in fluid communication with the lower-pressure fluid source and configured to open when the second pressure exceeds a threshold.

13. The method of claim 10, wherein the lower-pressure fluid source comprises one of a bootstrap reservoir and a low-pressure accumulator.

14. The method of claim 10, wherein the high-pressure fluid source comprises a high-pressure accumulator to store the working fluid at the first pressure.

15. The method of claim 10, further comprising directing the working fluid used to selectively recruit the first subset of the plurality of actuators to the lower-pressure fluid source.

16. The method of claim 10, wherein the variable recruitment actuator system is comprised within a prosthetic device.

17. The method of claim 10, further comprising:
    providing a throttling valve disposed between the high-pressure fluid source and the plurality of actuators; and
    actuating, using the control system, the throttling valve to decrease the first pressure.

18. The method of claim 10, further comprising:
    generating, using a pressure transducer, a measure of pressure of the working fluid;
    providing a pump operable to increase the pressure of the working fluid; and
    selectively activating, using the control system, the pump based on the measure of pressure of the working fluid.

* * * * *